United States Patent [19]

DiLorenzo

[11] Patent Number: 4,760,383
[45] Date of Patent: Jul. 26, 1988

[54] ENURESIS TREATMENT SYSTEM

[76] Inventor: Daniel J. DiLorenzo, 109 Pearl Light Circle, Ft. Washington, Md. 20744

[21] Appl. No.: 939,628

[22] Filed: Dec. 8, 1986

[51] Int. Cl.⁴ ..................... G08B 23/00; A61B 19/00
[52] U.S. Cl. ............................. 340/573; 128/138 A; 340/604
[58] Field of Search ............................. 340/573, 604; 128/138 A; 200/61.04, 61.05

[56] References Cited

U.S. PATENT DOCUMENTS

| | | | |
|---|---|---|---|
| 3,460,123 | 8/1969 | Bass | 128/138 A |
| 4,191,950 | 3/1980 | Levin et al. | 340/604 |
| 4,212,295 | 7/1980 | Snyder | 340/573 X |
| 4,238,522 | 12/1980 | Potts | 128/90 X |
| 4,539,559 | 9/1985 | Kelly et al. | 340/573 |
| 4,653,491 | 3/1987 | Okada et al. | 340/573 X |

FOREIGN PATENT DOCUMENTS 8401626  4/1984  World Int. Prop. O. ...... 128/138 A

OTHER PUBLICATIONS

Boylestad et al., "Darlington Compound Configuration", *Electronic Devices and Circuit Theory*, 3rd ed., pp. 336–337, 1982.

Primary Examiner—Glen R. Swann, III
Assistant Examiner—Thomas J. Mullen, Jr.

[57] ABSTRACT

An improved moisture sensing device, incorporating a new type of sensor, represents a significant improvement in the performance of bedwetting detection devices. The sensor involved offers a substantial advance in the response time of the system as well as full sensitivity over the entire perineal area.

19 Claims, 2 Drawing Sheets

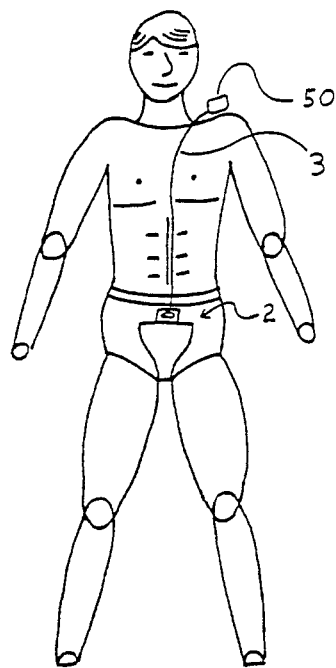
Fig #1
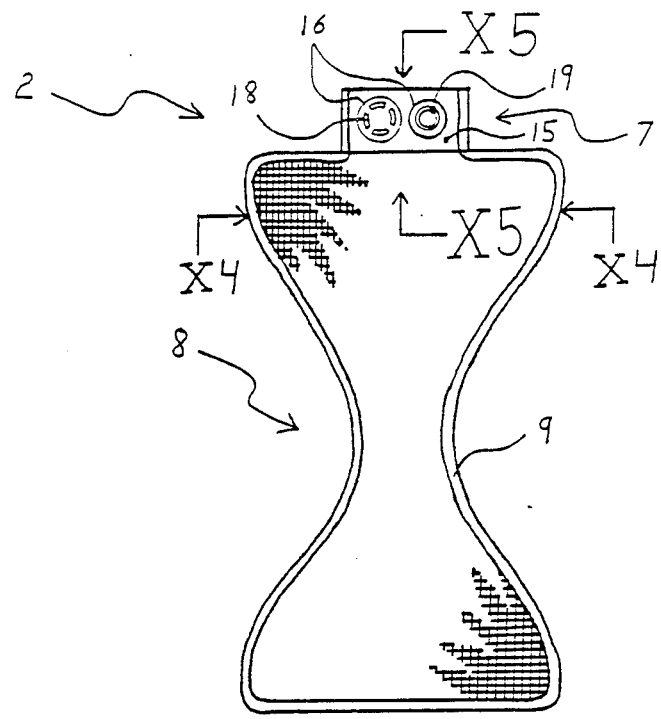
Fig #2
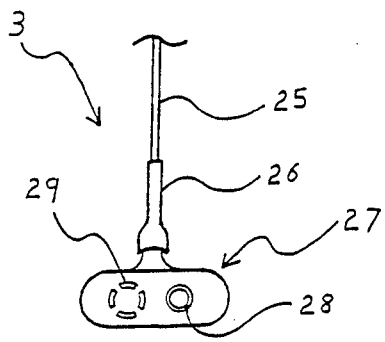
Fig #3
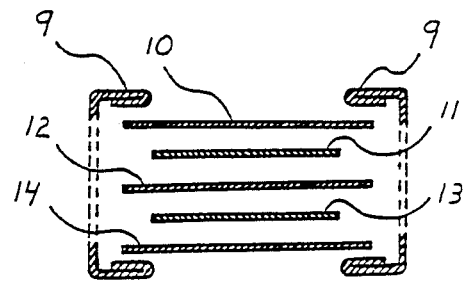
Fig #4

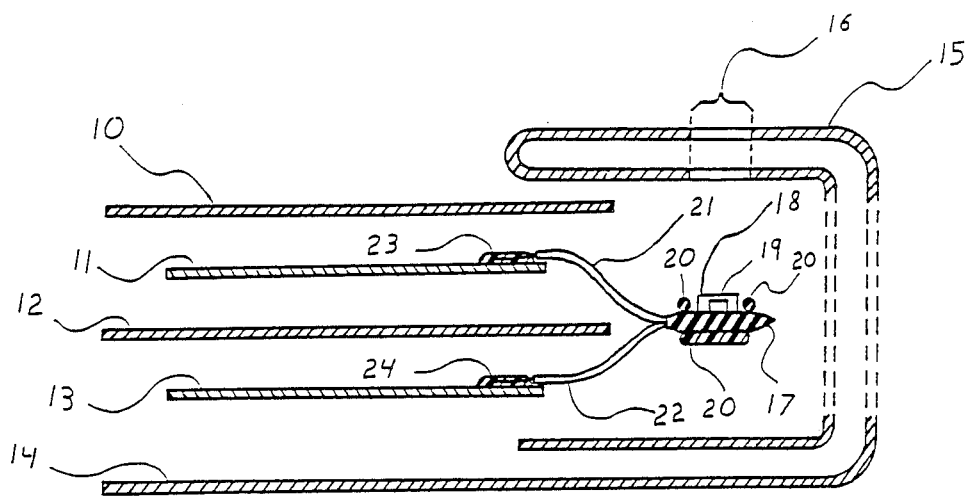
Fig #5
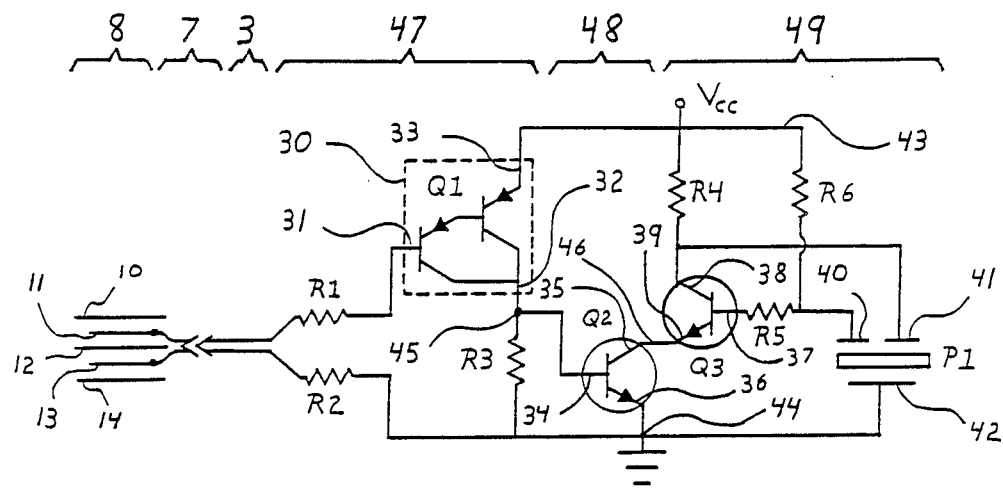
Fig #6

ENURESIS TREATMENT SYSTEM

BACKGROUND OF THE INVENTION

This invention relates to moisture sensing devices, and in particular to an improvement in devices for detecting urine and awaking enuretic children and adults.

Enuresis, particularly of the nocturnal type poses a vexing problem that is common especially among children and adolescents as well as among the elderly. Not surprisingly, many of those affected by enuresis are deep sleepers. Numerous devices have been proposed to sense the occurrence of bedwetting and to awaken the user upon the discovery thereof. Early such devices involved placing under the user's bed a sheet of a water permeable insulate, such as cotton, sandwiched by two pieces of metal foil, of which the top foil was perforated to allow the passage of urine. Upon wetting with electrolytic urine, the insulating layer becomes conductive and with suitable electronics, an alarm is sounded, awakening the user. Most recent such inventions are of a portable type, to be worn by the user within or in place of his undergarments. These offer the advantage of an improved response time, that is, they exhibit a shorter lag time between urination onset and its detection. These portable versions have several drawbacks, the overcoming of which is the object of the present invention. First is the limited area of detection imposed by such portable sensors. Buttonlike sensors, such as those described in U.S. Pat. Nos. 4,271,406 and 3,530,855 exhibit the highest vulnerability to being entirely missed by the flow of urine, especially for boys. Similarly, strip sensors, such as that presented in U.S. Pat. No. 4,191,950, do not provide sensitivity over the entire perineal area. Second, is the degraded response time presented by sensors which do not cover the entire perineal area. Such sensors depend on a lateral urine flow across the perineal area to the active area of the sensor. This can present a considerable delay in cases of sensor misalignment, a problem particularly pronounced with boys. This is a special problem for small sensors, such as the buttonlike sensors previously mentioned, as well as for larger sensors which do not maintain sensitivity throughout the full area of the sensor, such as the edge-sensitive strip described in the preferred embodiment of U.S. Pat. No. 4,191,950. Third, is the drawback that many previous designs incur higher production costs due to sensor complexity and to special processing involved in the fabrication thereof, the perforation of conductive layers being particular among these.

SUMMARY OF THE INVENTION

The present invention is comprised of a urine detecting sensor assembly 2, an electrical circuit 6 which activates an alarm upon detecting urine across the said sensor 2, and a means 3 for electrically connecting said circuit 6 to the sensor assembly 2. The said sensor 2 is innovative in that it provides fast response time, sensitivity over the entire perineal area, is inexpensive to fabricate, and is inherently comfortable to wear in that the sensor pad 8 which spans the perineal region is constructed entirely of fabric. The means 3 of electrically connecting the sensor assembly 2 to the electrical circuitry 6 offers the advantages of low manufacturing costs, small size and low profile, ease of manually connecting the connector plugs 27 and 17, and comfort to the user. The electrical circuit 6, as provided herein, offers simplicity, resulting in compactness, high reliability, and incurrence of low manufacturing costs.

BRIEF DESCRIPTION OF THE DRAWINGS

FIG. 1 is a drawing of the moisture sensor assembly 2, the electrical connection means 3, and the electrical circuit 6 contained within the circuit enclosure 50 shown worn by a child being trained;

FIG. 2 is a drawing of the sensor assembly 2 with its sensor pad region 8 and electrical connection tab 7;

FIG. 3 is a drawing of the electrical connection cable assembly 3 providing a means of connection between the electronic circuit 6 and the sensor assembly 2;

FIG. 4 is a cross sectional view of the sensor pad 8 in FIG. 2 taken along the line X4—X4;

FIG. 5 is an exploded cross sectional view of the electrical connection tab 7 and part of the sensor pad 8 in FIG. 2 taken along the line X5—X5; and FIG. 6 is the preferred embodiment of a conductivity detecting electrical circuit 6.

DESCRIPTION OF THE PREFERRED EMBODIMENT

As shown in FIG. 1 of the drawings, a child may wear pants which support by containment against the user's body the sensor assembly 2 to be described later in this invention. The sensor assembly 2 may also be worn within any other form of supportive covering, including but not limited to a diaper, pamper, or pajama pants. In addition, the sensor assembly 2 may be permanently affixed to an article of clothing or any other supportive covering by any means of connection, including but not limited to stitching, adhesive bonding, use of mechanical snaps, or by Velcro strips. In the preferred embodiment, the sensor assembly 2 remains free of any mechanical affixation to clothing; but it is comfortably tucked within snug clothing such as underpants or a diaper of either the cloth or disposable type. Also shown in FIG. 1 is the electrical circuit enclosure 50 and the electrical connection cable 3 by which the electrical circuit 6 is connected to the sensor assembly 2. The said circuit 6 may be mounted by any suitable means such as an elastic strap, a Velcro belt, or a clothing pin on a convenient location on the user's body or garments. Such locations include but are not limited to the inside of user's leg, the user's arm, or the user's shoulder.

The periphery of the sensor pad 8, shown in FIG. 2 is covered by a strip of bordering trim 9; in the preferred embodiment, this trim 9 takes the form of bias tape, but any other form of trim may be used. Affixed to the sensor pad 8 is the means 7 of providing a suitable electrical connection. This is implemented by a 9 volt battery type plug 17; however, other electrical connectors may be used. The electrical connectors 18 and 19 protrude through an appropriate opening 16 in the fabric covering 15 of the electrical connection tab 7. This opening 16 may take any suitable form, such as two separate circular openings or a single oval opening in the connector's fabric covering 15.

The electrical connection to the sensor is completed by means of a mating connector 27 at the end of a cord 25 of suitable length for the chosen mounting site for the electrical circuit 6. To insure long operational life, a strain relief 26 is provided between the body of the connector 27 and the said cord 25. In the accompanying drawings, cable connectors 28 and 29 will mate with said sensor connectors 18 and 19 respectively. This polarity is by no means critical; the sensor connection would be equally as effective if the means of connection was nonpolarized.

The sensor pad 1 is a five layer assembly, the cross section of which is depicted in exploded form in FIG. 4. Three insulating layers 10, 12, and 14, are placed alternately with two electrically conducting layers 11 and 13. The said insulating layers 10, 12, and 14 are constructed of a highly water permeable material, preferrably of cotton due to its favorable cost and comfort attributes. In the preferred embodiment, the said electrically conducting layers 11 and 13 are made of a silver impregnated nylon knit with relatively large cell sizes, typically of one eighth of an inch. These electrically conductive nylon knit layers 11 and 13, being more than readily permeable to water, offer virtually no impedance to the flow of urine through the sensor pad 8. This is a key design feature contributing to the improved response time of the sensor pad 8 proclaimed in this invention. By using such a material, the cost of perforating an otherwise water impervious electrically conductive layer is bypassed. In the preferred embodiment, conductive layers 11 and 13 are given a permanent coating of Melamine, offering increased resistance to tearing and maintaining constant cell size of the knit, thereby making handling of the material easier during sensor fabrication as well as contributing to the overall ruggedness of the sensor pad 8. This material offers the added benefit of readily conforming to the curves of the user's body without wrinkling or bunching up, providing a snug form fit without sacrificing the comfort of the user. The said trim 9 of bias tape provides structural continuity while maintaining an aesthetically pleasing appearance.

The means 3 of providing electrical connection to the sensor assembly 2 is shown in the exploded drawing presented in FIG. 5. A compact low profile plug 17 such as a 9 volt battery clip is enclosed within a protective covering 15, implemented in the preferred embodiment as a bilayer of cloth, a doubly folded extension of the outer insulating layer 14. This covering 15 could be fabricated as an extension of the other outer insulating layer 10 or as an entirely separate piece to be stitched or otherwise affixed to the sensor pad 8. The connector plug 17 is secured within the connector plug covering 15 of the sensor by any of several means 20, including but not limited to a silicone or epoxy adhesive, stitching, stapling, or riveting. In the preferred embodiment, this securing means 20 takes the form of a flexible silicone adhesive, maintaining the overall physical flexibility of the sensor assembly. The conducting leads 21 and 22 of the sensor connector plug 17 are connected to the conductive layers 11 and 13 respectively of the sensor pad 8. As previously noted, this connection scheme may be reversed in polarity due to the nonpolar nature of the sensor pad 8. These electrical connections may be accomplished through any suitable means 23 and 24 respectively, including but not limited to riveting, stapling, or the use of an electrically conductive adhesive, as proscribed in the preferred embodiment and shown in FIG. 5.

A conductivity detecting electrical circuit 6, such as that diagrammed in FIG. 6, is electrically connected to the said conductive layers 11 and 13 of the sensor pad 8 by means of a cable assembly 3 and the electrical connection tab 7. Various alarm circuits can be used with the sensor assembly 2 provided in this invention. Typically, this circuit will have three stages, the first being a high impedance detection stage 47, the second being an amplifying and switching stage 48 which will switch on a third stage 49, and the third stage 49 being an oscillator providing an audio frequency output. The said second stage 48 may also possess a low frequency oscillator, modulating the audio frequency output of the third stage 49. A typical modulation frequency would be between 1 and 10 Hertz, increasing the effectiveness of the alarm in awakening the user. In FIG. 6, the preferred embodiment of this circuit 6 is diagrammed. The detector stage 47 consists of R1, R2, R3, and Q1. The +9 volt battery terminal 43 is connected to the emitter 33 of PNP Darlington Transistor Pair Q1 indicated within the dotted line 30. The base 31 of Q1 is connected through base resistor R1 to conductive layer 11 of the sensor pad 8. The other conductive layer 13 is connected through R2 to the ground terminal 44. Again, the connection scheme of conductive layers 11 and 13 can be reversed. The collector 32 of Q1 passes through gain resistor R3 to the ground terminal 44. Characteristic of this detector stage is the Darlington Transistor Pair Q1, providing very high input impedance, insuring a minimal current passing through the sensor pad 8 upon wetting with urine. Q1 base resistor R1 and ground resistor R2 limit the current through the sensor pad 8 to a miniscule level. Redundancy of resistors R1 and R2 provides a safety factor should one of the two become shorted or bypassed due to defective manufacture or other unexpected reason. This virtually eliminates any chance of discomfort to the user due to a larger than anticipated electric current flowing through the sensor pad 8 upon wetting with urine. The amplifying and switching stage 48 is comprised of NPN transistor Q2. The collector 32 of Q1 provides the input at the junction 45 to this second stage 48, being connected to the base 34 of NPN transistor Q2. The emitter 36 of Q2 is connected to ground 44. The interface between the amplifying and switching stage 48 and the audio oscillator stage 49 occurs at the junction 46. At this junction 46, the collector 35 of Q2 functions as a current sink, connected to the emitter 39 of NPN transistor Q3. The audio output stage 49 is comprised of R4, R5, R6, Q3, and P1. To provide for compactness, low power consumption, and simplified drive circuitry, a piezoelectric audio transducer P1 is used as the buzzing element. One side of gain resistor R4 is connected to the +9 volt battery terminal 43, while the other end is connected the collector 38 of Q3 and to the drive tab 41 of piezoelectric audio transducer P1. The feedback tab 40 of P1 is connected to R6, the other end of which connects to the +9 volt battery terminal 43, and to base resistor R5 which connects to the base 37 of Q3. The ground tab 42 of P1 is connected to the circuit ground 44, being connected to the emitter 36 of Q2, to R3, and to R2.

With no signal present, i.e. a dry sensor pad 8, all three transistors Q1, Q2, and Q3 are cut off; this insures that no current, with the exception of the transistor leakage currents amounting to a few microamperes, flows when the sensor pad 8 is dry. With such a circuit 6, a typical 9 volt battery will last several months with a dry or disconnected sensor pad 8. This justifies the omission of an on-off switch, further reducing production costs.

When insulating layer 12 of the sensor pad 8 is wetted with urine, current flows from the base 31 of Q1 through R1, the wetted sensor pad 8, and R2, turning Q1 on. This causes the collector 32 of Q1 to go positive, similarly bringing up the voltage at the junction 45 and the base 34 of Q2, turning Q2 on. With Q2 in the fully on or saturated state, the audio output stage 49 is free to oscillate, producing an audio output, promptly awakening the user.

CONCLUSION

There has been set forth hereinbefore, an innovative enuretic control device operative to provide an audible tone to awaken the user upon detection of urination with a negligible delay time between urination onset and its detection. In one specific embodiment disclosed herein, the arrangement is utilized to provide complete portable operation with no discomfort to the user.

While such arrangement has particular utility to the treatment of enuresis, it will be apparent to parties skilled in the art that similar advantages attain in the use of the equipment in numerous other applications requiring small, lightweight, mechanically flexible detection of moisture.

While what is described is regarded as the preferred embodiment of the invention, nevertheless it will be understood that such illustration is merely exemplary and that numerous modifications may be made therein without departing from the essence of the invention.

I claim:

1. An improved device for detecting unintentional urination worn over a user's perineal area, comprising:
   an elongated, moisture responsive sensor pad having two electrically conductive, water-permeable fabric layers sandwiched among three water absorbant, electrically non-conductive layers of fabric, and having an electrical connection tab with two conducting leads each of which interconnects a separate said electrically conductive layer with a separate external electrical contact on the said tab;
   an audio alarm;
   electrical circuit means having a high impedance detection stage with two input resistors, each of which corresponds to a said electrically conductive layer, and having an amplifier and switching stage connected to said impedance detection section, said amplifier and switching stage driving an audio output stage activating said audio alarm upon detection of moisture by said sensor pad, said electrical circuit means having no current flow when said pad is dry; and
   a cable assembly interconnecting said electrical connection tab external electrical contacts individually in series with a separate impedance detection section input resistor.

2. A device as recited in claim 1 wherein:
the electrically conductive, water-permeable fabric layers are made of a silver-impregnated, nylon knit with relatively large knit cell sizes.

3. A device as recited in claim 2 wherein:
the said knit cell sizes are in the order of one-eighth inch in size.

4. A device as recited in claim 3 wherein:
the electrically conductive, water-permeable fabric layers have a permanent coating of Melamine to resist tearing and to maintain constant knit cell size.

5. A device as recited in claim 4 wherein:
upon the said sensor pad becoming moist, a current will flow across the said electrically conductive fabric layers.

6. A device as recited in claim 5 wherein:
said current flow will generate a signal across said cable assembly to said electrical circuit means detection stage.

7. A device as recited in claim 6 wherein:
a Darlington transistor pair is employed to provide high input impedance to the said detection stage.

8. A device as recited in claim 7 wherein:
upon said detection stage detecting a signal, the amplifying and switching stage will activate the audio output stage of said electrical circuit means.

9. A device as recited in claim 8 wherein:
said audio output stage comprises a free oscillating feedback driven, piezoelectric audio transducer drive circuit.

10. A device as recited in claim 9 wherein:
said amplifying and switching stage turns on the audio output stage when said sensor pad becomes moist and the high impedance detector stage detects a signal.

11. A device as recited in claim 10 wherein:
said amplifying and switching stage is an NPN transistor with its base connected to the detector stage, its emitter grounded, and its collector connected to the audio output stage.

12. A device as recited in claim 11 wherein:
said audio output stage includes an NPN transistor appropriately configured to drive a piezoelectric audio transducer included within said audio output stage.

13. A device as recited in claim 12 wherein:
said Darlington transistor pair, said amplifier and switching stage transistor, and said audio output stage transistor are cut off without current flow when said sensor pad is dry.

14. A device as recited in claim 13 wherein:
the collector of said amplifying and switching stage NPN transistor functions as a current sink connected to the emitter of said audio output stage NPN transistor.

15. A device as recited in claim 14 wherein:
said Darlington transistor pair is a PNP pair whose collector is connected to the base of said amplifying and switching stage NPN transistor.

16. A device as recited in claim 15 wherein:
the base of said PNP Darlington transistor pair is connected through one of said detection stage input resistors to one of said electrically connected sensor pad conductive layers.

17. A device as recited in claim 16 wherein:
a battery power source with two terminals, one grounded and one ungrounded, is connected across said electrical circuit means.

18. A device as recited in claim 17 wherein:
the emitter of said PNP Darlington transistor pair is connected to the ungrounded terminal of said battery power source.

19. A device as recited in claim 18 wherein:
the collector of said audio output stage NPN transistor is connected via a gain resistor to the ungrounded terminal of said battery power source.

* * * * *